United States Patent
Isele et al.

(10) Patent No.: US 9,464,369 B2
(45) Date of Patent: **\*Oct. 11, 2016**

(54) ARTICLES CONTAINING NANOFIBERS FOR USE AS BARRIERS

(75) Inventors: Olaf Erik Alexander Isele, West Chester, OH (US); Rajeev Chhabra, Mason, OH (US); Han Xu, West Chester, OH (US); Srinivas Krishnaswany Mirle, Liberty Township, OH (US); Eric Bryan Bond, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 385 days.

This patent is subject to a terminal disclaimer.

(21) Appl. No.: 11/109,557

(22) Filed: Apr. 19, 2005

(65) Prior Publication Data

US 2006/0014460 A1    Jan. 19, 2006

Related U.S. Application Data

(60) Provisional application No. 60/563,346, filed on Apr. 19, 2004.

(51) Int. Cl.
*A61F 13/15* (2006.01)
*D01D 5/42* (2006.01)
(Continued)

(52) U.S. Cl.
CPC ......... *D01D 5/423* (2013.01); *A61F 13/15203* (2013.01); *A61F 13/51401* (2013.01);
(Continued)

(58) Field of Classification Search
CPC . A61F 13/15; A61F 13/15203; D04H 1/728; B32B 27/12

USPC ................. 442/340, 354, 334, 327
See application file for complete search history.

(56) References Cited

U.S. PATENT DOCUMENTS

3,280,229 A    10/1966  Simons
3,475,198 A    10/1969  Drum
(Continued)

FOREIGN PATENT DOCUMENTS

JP    Hei 01-156561    6/1989
JP    3249207 A2    11/1991
(Continued)

OTHER PUBLICATIONS

U.S. Appl. No. 10/877,538, Isele, et al., filed Jun. 25, 2004.
(Continued)

*Primary Examiner* — Peter Y Choi
(74) *Attorney, Agent, or Firm* — Wednesday G. Shipp (57) ABSTRACT

The present invention is directed to articles comprising nanofibers. Preferred articles include diapers, training pants, adult incontinence pads, catamenials products such as feminine care pads and pantiliners, tampons, personal cleansing articles, personal care articles, and personal care wipes including baby wipes, facial wipes, body wipes, and feminine wipes. The nanofiber webs can be used as a barrier, wipe, absorbent material, and other uses.

The nanofibers, having a diameter of less than 1 micron, must comprise a significant number of the fibers in at least one nanofiber layer of the nonwoven web. The nonwoven web may have a hydrohead to basis weight ratio of greater than about 10 mbar/gsm. The nanofibers may be produced from a melt film fibrillation process.

38 Claims, 2 Drawing Sheets

(51) Int. Cl.

| | | |
|---|---|---|
| *A61F 13/514* | (2006.01) | |
| *D04H 13/02* | (2006.01) | |
| *D04H 1/4382* | (2012.01) | |
| *D04H 1/728* | (2012.01) | |
| *A61F 13/494* | (2006.01) | |
| *A61F 13/53* | (2006.01) | |

(52) U.S. Cl.
 CPC ....... *A61F13/51458* (2013.01); *D04H 1/4382* (2013.01); *D04H 1/728* (2013.01); *D04H 13/02* (2013.01); *A61F 13/494* (2013.01); *A61F 2013/15406* (2013.01); *A61F 2013/15447* (2013.01); *A61F 2013/15552* (2013.01); *A61F 2013/51452* (2013.01); *A61F 2013/530138* (2013.01); *B01D 2239/025* (2013.01); *Y10T 442/20* (2015.04); *Y10T 442/2213* (2015.04); *Y10T 442/60* (2015.04)

(56) References Cited

U.S. PATENT DOCUMENTS

| | | | |
|---|---|---|---|
| 3,806,289 A | 4/1974 | Schwarz | |
| 3,849,241 A | 11/1974 | Butin et al. | |
| 3,972,759 A | 8/1976 | Buntin | |
| 4,100,324 A | 7/1978 | Anderson et al. | |
| 4,536,361 A | 8/1985 | Torobin | |
| 4,587,154 A | 5/1986 | Hotchkiss et al. | |
| 4,713,068 A | 12/1987 | Wang et al. | |
| 4,753,843 A | 6/1988 | Cook et al. | |
| 4,784,892 A | 11/1988 | Storey et al. | |
| 4,818,464 A | 4/1989 | Lau | |
| 4,824,451 A | 4/1989 | Vogt et al. | |
| 4,869,275 A | 9/1989 | Berger | |
| 4,874,666 A | 10/1989 | Kubo et al. | |
| 4,919,810 A | 4/1990 | Itoh et al. | |
| 4,923,454 A | 5/1990 | Seymour et al. | |
| 4,937,020 A | 6/1990 | Wagner et al. | |
| 4,973,325 A | 11/1990 | Sherrod et al. | |
| 4,980,215 A | 12/1990 | Schonbrun | |
| 5,039,727 A | 8/1991 | Onishi et al. | |
| 5,075,161 A | 12/1991 | Nyssen et al. | |
| 5,108,820 A | 4/1992 | Kaneko et al. | |
| 5,114,631 A | 5/1992 | Nyssen et al. | |
| 5,137,600 A | 8/1992 | Barnes et al. | |
| 5,183,670 A | 2/1993 | Trudeau et al. | |
| 5,192,468 A | 3/1993 | Coates et al. | |
| 5,213,881 A | 5/1993 | Timmons et al. | |
| 5,244,482 A | 9/1993 | Hassenboehler et al. | |
| 5,260,003 A | 11/1993 | Nyssen et al. | |
| 5,290,626 A | 3/1994 | Nishioi et al. | |
| 5,464,688 A | 11/1995 | Timmons et al. | |
| 5,482,765 A | 1/1996 | Bradley et al. | |
| 5,487,943 A | 1/1996 | Kozulla | |
| 5,518,801 A | 5/1996 | Chappell et al. | |
| 5,679,042 A | 10/1997 | Varona | |
| 5,679,379 A | 10/1997 | Fabbricante et al. | |
| 5,681,646 A | 10/1997 | Ofosu et al. | |
| 5,695,849 A * | 12/1997 | Shawver et al. | 428/131 |
| 5,700,254 A | 12/1997 | McDowall et al. | |
| 5,733,822 A | 3/1998 | Gessner et al. | |
| 5,843,056 A | 12/1998 | Good et al. | |
| 5,885,269 A | 3/1999 | Boyer et al. | |
| 5,885,681 A | 3/1999 | Korpman | |
| 5,910,368 A | 6/1999 | Ehret | |
| 5,935,883 A | 8/1999 | Pike et al. | |
| 5,939,467 A | 8/1999 | Wnuk et al. | |
| 5,977,250 A | 11/1999 | George et al. | |
| 5,994,482 A | 11/1999 | Georgellis et al. | |
| 6,110,588 A | 8/2000 | Perez et al. | |
| 6,114,017 A | 9/2000 | Fabbricante et al. | |
| 6,183,670 B1 | 2/2001 | Torobin et al. | |
| 6,187,699 B1 | 2/2001 | Terakawa et al. | |
| 6,258,997 B1 | 7/2001 | Johansson et al. | |
| 6,265,333 B1 * | 7/2001 | Dzenis et al. | 442/346 |
| 6,269,513 B1 | 8/2001 | Torobin | |
| 6,284,680 B1 * | 9/2001 | Aikawa et al. | 442/363 |
| 6,315,806 B1 | 11/2001 | Torobin et al. | |
| 6,331,343 B1 | 12/2001 | Perez et al. | |
| 6,350,711 B1 | 2/2002 | Potts et al. | |
| 6,382,526 B1 | 5/2002 | Reneker et al. | |
| 6,395,046 B1 | 5/2002 | Emig et al. | |
| 6,432,347 B1 | 8/2002 | Perez et al. | |
| 6,464,994 B1 | 10/2002 | Moehring | |
| 6,488,801 B1 | 12/2002 | Bodaghi et al. | |
| 6,494,974 B2 | 12/2002 | Riddell | |
| 6,520,425 B1 | 2/2003 | Reneker | |
| 6,613,703 B1 | 9/2003 | Yahiaoui et al. | |
| 6,692,823 B2 | 2/2004 | Kody et al. | |
| 6,695,992 B2 | 2/2004 | Reneker | |
| 6,706,086 B2 * | 3/2004 | Emig et al. | 55/486 |
| 6,872,311 B2 | 3/2005 | Koslow | |
| 6,878,650 B2 | 4/2005 | Clark et al. | |
| 6,924,028 B2 * | 8/2005 | Chung et al. | 428/357 |
| 7,097,904 B2 | 8/2006 | Ochi et al. | |
| 7,267,789 B2 | 9/2007 | Chhabra et al. | |
| 7,291,300 B2 | 11/2007 | Chhabra et al. | |
| 7,390,760 B1 | 6/2008 | Chen et al. | |
| 7,576,019 B2 | 8/2009 | Bond et al. | |
| 7,989,369 B2 | 8/2011 | Bond et al. | |
| 2002/0006434 A1 | 1/2002 | Shanklin et al. | |
| 2002/0035354 A1 * | 3/2002 | Mirle et al. | 604/385.01 |
| 2002/0046656 A1 | 4/2002 | Benson et al. | |
| 2002/0096246 A1 | 7/2002 | Sennet et al. | |
| 2002/0110655 A1 | 8/2002 | Seth | |
| 2002/0117782 A1 | 8/2002 | Haynes et al. | |
| 2002/0129834 A1 | 9/2002 | Bailey | |
| 2002/0148050 A1 | 10/2002 | Luo et al. | |
| 2003/0065298 A1 | 4/2003 | Krishnaswamy-Mirle et al. | |
| 2003/0129909 A1 | 7/2003 | Zucker | |
| 2003/0168401 A1 | 9/2003 | Koslow | |
| 2003/0177909 A1 | 9/2003 | Koslow | |
| 2004/0002273 A1 | 1/2004 | Fitting et al. | |
| 2004/0031749 A1 * | 2/2004 | Koslow | 210/505 |
| 2004/0038013 A1 | 2/2004 | Schaefer et al. | |
| 2004/0070118 A1 | 4/2004 | Czado | |
| 2004/0092185 A1 * | 5/2004 | Grafe et al. | 442/153 |
| 2004/0116028 A1 * | 6/2004 | Bryner | 442/381 |
| 2004/0131820 A1 | 7/2004 | Turner et al. | |
| 2004/0223040 A1 | 11/2004 | Graham et al. | |
| 2004/0266300 A1 | 12/2004 | Isele et al. | |
| 2005/0008776 A1 * | 1/2005 | Chhabra et al. | 427/180 |
| 2005/0053782 A1 | 3/2005 | Sen et al. | |
| 2005/0070866 A1 * | 3/2005 | Isele et al. | 604/367 |
| 2006/0014460 A1 | 1/2006 | Isele et al. | |
| 2006/0057350 A1 | 3/2006 | Ochi et al. | |
| 2006/0057922 A1 | 3/2006 | Bond et al. | |
| 2006/0084340 A1 | 4/2006 | Bond et al. | |
| 2006/0094320 A1 | 5/2006 | Chen et al. | |
| 2006/0153904 A1 | 7/2006 | Smith et al. | |
| 2007/0021021 A1 | 1/2007 | Verdegan et al. | |
| 2010/0305529 A1 | 12/2010 | Ashton et al. | |
| 2011/0196325 A1 | 8/2011 | Isele et al. | |
| 2011/0196327 A1 | 8/2011 | Chhabra et al. | |
| 2011/0196332 A1 | 8/2011 | Cheng et al. | |

FOREIGN PATENT DOCUMENTS

| | | |
|---|---|---|
| JP | 06-192953 | 7/1994 |
| JP | 06-192954 | 7/1994 |
| JP | 08-144166 A | 6/1996 |
| JP | 2668963 B2 | 10/1997 |
| JP | 2001-104372 A | 4/2001 |
| JP | 2002-201560 | 7/2002 |
| WO | WO-97/05306 | 2/1997 |
| WO | WO 00/44411 | 8/2000 |
| WO | WO 00/71797 A1 | 11/2000 |
| WO | WO 01/00124 A1 | 1/2001 |
| WO | WO-01/09425 A1 | 2/2001 |
| WO | WO-02092339 A1 | 11/2002 |
| WO | WO 03/043809 A1 | 5/2003 |
| WO | WO-03086234 A | 10/2003 |
| WO | WO 2004/020722 A2 | 3/2004 |
| WO | WO-2004/026167 A2 | 4/2004 |

(56) References Cited

FOREIGN PATENT DOCUMENTS

| WO | WO-2005004769 A | 1/2005 |
|---|---|---|
| WO | WO-2005005704 | 1/2005 |
| WO | WO-2005/103357 A1 | 11/2005 |

OTHER PUBLICATIONS

U.S. Appl. No. 10/877,540, Isele, et al., filed Jun. 25, 2004.
U.S. Appl. No. 10/877,458, Isele, et al., filed Jun. 25, 2004.
U.S. Appl. No. 10/877,462, Chhabra, et al., filed Jun. 25, 2004.
U.S. Appl. No. 10/877,463, Chhabra, et al., filed Sep. 10, 2004.
U.S. Appl. No. 11/109,554, Bond, et al., filed Apr. 19, 2005.
U.S. Appl. No. 11/109,393, Bond, et al., filed Apr. 19, 2005.
Fiber Handbook, Raw Materials, III. Production section (II), Edited by the Fiber Society, Maruzen Co., Ltd.
International Search Report dated Aug. 26, 2005, 9 pages.
U.S. Appl. No. 13/024,826, filed Feb. 10, 2011, Olaf Isele et al.
U.S. Appl. No. 13/024,844, filed Feb. 10, 2011, Rajeev Chhabra et al.
U.S. Appl. No. 13/024,858, filed Feb. 10, 2011, Calvin Hoi Wung Cheng et al.
Notice of opposition to a European patent filed by Fiberweb Corovin GmbH, filed Nov. 25, 2011, 38 pages.
Notice of opposition to a European patent filed by Borealis AG, filed Dec. 2, 2011, 25 pages.
Notice of opposition to a European patent filed by Paul-Hartmann-AG, filed Nov. 28, 2011, 14 pages.

\* cited by examiner

ARTICLES CONTAINING NANOFIBERS FOR USE AS BARRIERS

CROSS-REFERENCE TO RELATED APPLICATIONS

This application claims the benefit of U.S. Provisional Application No. 60/563,346, filed Apr. 19, 2004.

FIELD OF THE INVENTION

The present invention relates to articles made from nanofibers and the barrier performance of the articles.

BACKGROUND OF THE INVENTION

The need for articles produced from nonwoven containing nanofibers has continued to increase. The diameters of nanofibers are generally understood to be less than about 1000 nanometer or one micron. The nanofibers webs are desired due to their high surface area, low pore size, and other characteristics. The nanofibers, also commonly called microfibers or very fine fibers, can be produced by a variety of methods and from a variety of materials. Although several methods have been used, there are drawbacks to each of the methods and producing cost effective nanofibers has been difficult.

Methods of producing nanofibers include a class of methods described by melt fibrillation. Non limiting examples of melt fibrillation methods include melt blowing, melt fiber bursting, and melt film fibrillation. Methods of producing nanofibers, not from melts, are film fibrillation, electrospinning, and solution spinning. Other methods of producing nanofibers include spinning a larger diameter bi-component fiber in an islands-in-the-sea, segmented pie, or other configuration where the fiber is then further processed so that nanofibers result.

Melt fibrillation is a general class of making fibers defined in that one or more polymers are molten and extruded into many possible configurations (e.g. co-extrusion, homogeneous or bicomponent films or filaments) and then fibrillated or fiberized into filaments.

Melt blowing is a commonly used method of producing fibers. Typical fiber diameters range from 2 to 8 micron. Melt blowing can be used to make fibers with smaller diameters but with considerable changes needed to the process. Commonly, redesigned nozzles and dies are needed. Examples of these include U.S. Pat. Nos. 5,679,379 and 6,114,017 by Fabbricante et al. and U.S. Pat. Nos. 5,260,003 and 5,114,631 by Nyssen et al. These methods utilize relatively high pressures, temperatures, and velocities to achieve the small fiber diameter.

Melt fiber bursting is a derivative of mineral fiber making process that has been applied to polymer fiber making. Examples of mineral melt fiber bursting process include U.S. Pat. No. 4,001,357 by Walz et al. and U.S. Pat. Nos. 4,337,074 and 4,533,376 by Muschelknautz et al. The key to this process is the use of sonic and supersonic air (gas) velocities to burst the melt filament into a multiplicity of fine fibers. Typical fiber diameters range from less than 1 micron to about 6 micron. Examples of processes with bursting polymer melt into fine fibers include U.S. Pat. No. 5,075,161 by Nyssen et al.; European Patent Nos. 1 192 301 B1 and 0 724 029 B1 and European Patent Application 1 358 369 A2 by Gerking; and WO 04/020722 by Sodemann et al. These methods utilize Laval nozzles to speed up the gas velocities to sonic and/or supersonic range. When polymer melt is exposed to such high gas velocities, it bursts into multiplicity of fine fibers. The processes are configured by use of desired process conditions and die and nozzle geometries to produce desired fiber sizes.

Melt film fibrillation is another method to produce fibers. A melt film is produced from the melt and then a fluid is used to form nanofibers from the melt film. Two examples of this method include Torobin's U.S. Pat. Nos. 6,315,806; 5,183,670; and 4,536,361; and Reneker's U.S. Pat. Nos. 6,382,526, 6,520,425 and 6,695,992, assigned to the University of Akron.

Film fibrillation is another method of producing nanofibers although not designed for the production of polymeric nanofibers to be used in nonwoven webs. U.S. Pat. No. 6,110,588 by Perez et al., assigned to 3M, describes of method of imparting fluid energy to a surface of a highly oriented, highly crystalline, melt-processed, solidified polymer film to form nanofibers. The films and fibers are useful for high strength applications such as reinforcement fibers for polymers or cast building materials such as concrete.

Electrospinning is a commonly used method of producing nanofibers. In this method, a polymer is dissolved in a solvent and placed in a chamber sealed at one end with a small opening in a necked down portion at the other end. A high voltage potential is then applied between the polymer solution and a collector near the open end of the chamber. The production rates of this process are very slow and fibers are typically produced in small quantities. Another spinning technique for producing nanofibers is solution or flash spinning which utilizes a solvent.

Two-step methods of producing nanofibers are also known. The first step is to spin a larger diameter multicomponent fiber in an islands-in-the-sea, segmented pie, or other configuration. The larger diameter multicomponent fiber is then split or the sea is dissolved so that nanofibers result in the second step. For example, U.S. Pat. No. 5,290,626 by Nishio et al., assigned to Chisso, and U.S. Pat. No. 5,935,883, by Pike et al., assigned to Kimberly-Clark, describe the islands-in-the-sea and segmented pie methods respectively. These processes involve two sequential steps, making the fibers and dividing the fibers.

To produce disposable articles containing nanofibers that are commercially advantageous, the cost of the nanofibers must be controlled. Equipment, process, process aids, and polymer costs can all be controlled. Therefore, it is an object of the invention to produce nanofibers which are low in cost.

It is also desired to form products containing nanofibers for a variety of uses and benefits. The uses include executions such as a diaper, wipe, and absorbent material, among other uses.

SUMMARY OF THE INVENTION

The present invention is directed to articles comprising nanofiber webs that are suitable as barriers. The articles can include hygiene, medical, industrial, filtration, and geotextile articles. Nonlimiting examples of hygiene articles include diapers, training pants, adult incontinence pads, catamenials products such as feminine care pads and pantiliners, tampons, personal cleansing articles, personal care articles, and personal care wipes including baby wipes, facial wipes, body wipes, and feminine wipes. In addition to the use as a barrier, the nanofiber webs can be used as a wipe, absorbent material, and other uses. Particularly, the nanofiber web can be used as a liquid barrier in a diaper as an outercover, leg cuff, or barrier layer. It may also be used as a wipe for reducing the gradient of liquid, controlling delivery of materials, and other uses.

The nanofibers, having a diameter of less than 1 micron, can comprise a significant number of the fibers, preferably greater than 50% of fibers, in one layer of the web contained by the article. The nanofibers can provide high barrier and good air permeability for a relatively low basis weight of the web.

Heretofore, uniform nanofiber webs with low basis weights made from commonly used polymers, such as polypropylene and polyethylene are very challenging to produce. Electrospinning is a common way to make nanofibers but not suitable for polyolefins such as polypropylene or polyethylene. Polystyrene can be used in electrospinning but is too brittle and will form beads. Additionally, electrospinning is not a suitable method for high speed production or for in-line processing with other layers for webs. Other methods to make nanofibers have been used but are not controlled enough to make low basis weight uniform webs. A uniform web is desired as any type of hole or non-uniformity may create an unacceptable barrier. Therefore, there is a great desire to produce a uniform low basis weight web comprising a significant number of nanofibers.

It is preferred to produce nonwoven webs containing at least one layer having a significant number, preferably greater than 50%, of fibers having diameter of less than one micron. It is also preferred that the nonwoven web have a hydrohead to nanofiber layer basis weight ratio of greater than about 10 mbar/gsm, preferably greater than about 15 mbar/gsm, more preferably greater than about 20 mbar/gsm and even more preferably greater than about 30 mbar/gsm. It may also be desired that the air permeability of the nonwoven web be greater than about 1 m/min, preferably greater than about 15 m/min, more preferably greater than about 30 m/min, and most preferably greater than about 75 m/min. The product of the hydrohead and air permeability is preferably at least about 750 mbar*meter per minute, more preferably greater than about 1000 mbar*meter per minute, even more preferably greater than about 2000 mbar*meter per minute, and most preferably greater than 3000 mbar*meter per minute. The product of the hydrohead and air permeability divided by the basis weight is typically greater than about 500 mbar*meter per minute per gsm, preferably greater than about 750 mbar*meter per minute per gsm, and most preferably greater than about 1000 mbar*meter per minute per gsm.

The barrier property can be measured by hydrostatic head, commonly called hydrohead measurements. The hydrohead can be greater than 10 mbar and typically from about 15 to about 150 mbar. The average fiber diameter of a significant number of fibers in the nanofiber layer of the web can be less than one micron and preferably from about 0.1 microns to 1 micron, more preferably from about 0.3 microns to about 0.9 microns. The basis weight of the nanofiber layer can be less than about 25 gsm, commonly from about 0.1 to about 15 gsm, preferably less than 10 gsm or 5 gsm. The nanofiber layer may have a basis weight in the range of from about 0.5 to about 3 gsm or from about 0.5 to about 1.5 gsm, depending upon use of the nonwoven web. The barrier is defined as a barrier to liquids, solids, and/or mixtures thereof. For specific execution, the barriers can be designed for certain surface tension liquids or other particular uses by further modifying the surface of the fiber and/or web with a coating designed to provide such a barrier. For example, the nonwoven web can be surface coated to improve barrier performance against low surface tension fluids.

The webs of the present invention may also provide controlled delivery of a substance during use. One example is the delivery of lotions in a wipe. The wipe can be designed to selectively control the barrier properties through the use of nanofibers. This can enable timed as well as regional delivery. The delivery of certain substances in a wipe containing multiple substances can also be achieved. For example, hydrophilic and hydrophobic liquids can be distributed as desired. The controlled delivery can also be of light as different regions of the web can allow different amounts of light to penetrate the web.

Web uniformity can be measured through several methods. Examples of uniformity metrics include low coefficient of variation of pore diameter, basis weight, air permeability, and/or opacity. Uniformity can also mean lack of fiber bundles or roping, or visible holes, or other such defects. Uniformity may also be evaluated by the hydrohead or other liquid barrier measurement of the web. A higher barrier score generally indicates a more uniform web.

Pore diameter can be determined by methods known to those skilled in the art. The mean pore diameter of the nanofiber layer is preferably less than about 15 microns, more preferably less than about 10 microns, and most preferably less than about 5 microns. The desired coefficient of variation for a uniform web can be less than 20%, preferably less than about 15%, and more preferably about 10% or less. The lack of roping can be measured by counting the number of ropes or bundles of fibers in a measured area of the web. The lack of holes can also be measured by counting the number of holes having a diameter above a certain threshold in a measured area of the web. A scanning electron microscope or other enlargement means can be used. For example, the holes may be counted if they are visible to the naked eye using a light box, or are more than 100 microns in diameter.

It may be desired to form a web of several layers. The nanofiber layer may be combined with one, two, or more layers. A spunbond-nanofiber-spunbond web is one example. Basis weights for the total composite webs range from about 5 gsm to about 100 and are commonly from about 10 to about 50 gsm.

Many of today's products utilize a barrier web comprising melt blown fibers. The average diameter of melt blown fibers is around 2 to 8 microns. Typically, melt blown webs will have a hydrohead to basis weight ratios of about 3 to 5 mbar/gsm. The basis weight of the melt blown web is commonly from about 2 to about 20 gsm. Air permeability is typically from about 0.1 to 100 m/min, depending on the method of web forming.

The nanofiber layer can be produced by any method resulting in a uniform layer of nanofibers. Preferably, the nanofibers are produced from a melt fibrillation process, more preferably from melt film fibrillation process. The melt film fibrillation process generally includes the steps of providing a polymeric melt, utilizing a central fluid stream to form a hollow polymeric film tube, and using this and/or other fluid streams to form multiple nanofibers from the hollow tube. The equipment may be designed to form a hollow tube of film at an orifice whereby a positive pressure fluid is blown through the center of the film subjecting it to a stretching and quenching process causing the viscosity of the film to increase and fibrillate once the local viscosity reaches a critical state defined by the material characteristics. The fibrillation and solidification may occur before the fibers and fluid exit the nozzle. The equipment may be designed so that the hollow polymeric film tube may have melt weakened regions to help induce fibrillation. An alternative apparatus of making nanofibers is a slot or slit type nozzle design which produces a thin, relatively flat film (instead of a hollow film tube) which results in nanofibers.

BRIEF DESCRIPTION OF THE DRAWINGS

While the specification concludes with claims pointing out and distinctly claiming the present invention, it is believed the same will be better understood by the following drawings taken in conjunction with the accompanying specification.

DETAILED DESCRIPTION OF THE INVENTION

The present invention relates to articles made from nanofibers. The nanofibers are produced from one or more thermoplastic polymers. Nonlimiting examples of thermoplastic polymers suitable for the present invention include polyolefins, polyesters, polyamides, polystyrenes, polyurethanes, biodegradable polymers including thermoplastic starch, PHA, PLA, starch compositions, and combinations thereof. The homopolymer, copolymers, and blends thereof are included within this description. The most preferred polymers are polyolefins such as polypropylene and polyethylene, nylons, and polyethylene terephthalate.

Suitable thermoplastic polymers include any polymer suitable for melt spinning. The rheological properties of the polymer must be such that the polymer can be melt extruded. The melting temperature of the polymer is generally from about 25° C. to 400° C. The polymers of the present invention may have a melt flow rate of less than about 400 decigrams per minute. This measurement is taken as the polymer is present in the die. The melt flow rate is measured using ASTM method D-1238. Preferably, the melt flow rate may be less than about 300 decigrams per minute, more preferably less than about 200 decigrams per minute, and most preferably less than about 100 decigrams per minute. A most preferred range for melt flow rates is from about 1 decigram per minute to about 100 decigrams per minute. Generally, the lower the melt flow rate the more preferred. Therefore, polymers with melt flow rates less than about 40 decigrams per minute may be utilized.

The fibers may be single- or multi-component fibers such as bicomponent fibers. The fibers may have a sheath-core or side-by-side or other suitable geometric configuration. After the fibers are made, the fibers may be treated or coated before formed into a web. Additionally, after a web is made, the web may be treated. Optionally, additives may be compounded into the polymer resin and these additives migrate out to the surface after the fibers are formed. The additives that move to the surface may need to be cured utilizing external energy, such as heat, or additives on surface may need to be chemically reacted with another component or curing may need to be catalyzed in the presence of another component, such that additional components may be added to the process while the fibers are being made or after the fibers are made using the resin with additives. Suitable treatments include hydrophilic or hydrophobic treatments. An example of hydrophobic treatment is poly-di-methyl-siloxanes. The specific treatment depends on the use of the web, type of polymer, and other factors. Desirable treatments are familiar to those skilled in the art.

Optionally, the polymer may contain additional materials to provide other properties for the fiber. These may modify the physical properties of the resulting fiber such as elasticity, strength, thermal or chemical stability, appearance, absorbency, odor absorbency, surface properties, and printability, among others. A suitable hydrophilic melt additive may be added. Optional materials may be present up to 50% of the total polymer composition.

The method of making the nanofibers of the present invention is preferably a melt fibrillation process, or more preferably a melt film fibrillation process. Generally, this process involves providing a polymeric melt, utilizing a central fluid stream to form a polymeric film, and then using a fluid to form multiple nanofibers from the film. Suitable methods are detailed, for example, in U.S. Pat. No. 4,536,361 to Torobin and U.S. Pat. Nos. 6,382,526, 5,520,425 and 6,695,992 to Reneker. The film may be a hollow tube, relatively flat, or other suitable structure.

As further described in U.S. Pat. No. 4,536,361, the polymer is heated until it forms a liquid and flows easily. The melted polymer may be at a temperature of from about 0° C. to about 400° C., preferably from about 10° C. to about 300° C., and more preferably from about 20° C. to about 220° C. The temperature of the polymer depends on the melting point of the polymer or polymer composition. The temperature of the polymer can be less than about 50° C. above its melting point, preferably less than 25° C. above its melting point, more preferably less than 15° C. above its melting point, and just at or above its melting point or melting range. The melting point or range is measured using ISO 3146 method. The melted polymer will typically have a viscosity of from about 1 Pa-s to about 1000 Pa-s, typically from about 2 to about 200 Pa-s and more commonly from about 4 to about 100 Pa-s. These viscosities are given over a shear rate ranging from about 100 to about 100,000 per second. The melted polymer is at a pressure of about atmospheric pressure or slightly elevated.

In one method, the fiberizing fluid may push through the polymer liquid film to form a hollow polymer tube by blowing and applying pressure on the film and then inner surface of the tube. In another method detailed in U.S. Pat. No. 6,695,992, the fiberizing fluid will form a sheet of thin film from a slit or slot type die design. The fiberizing fluid may be at a temperature close to the temperature of the melted polymer. Non-limiting examples of the fiberizing fluid are gases such as nitrogen or more preferably air. The fiberizing fluid temperature may be a higher temperature than the melted polymer to help in the flow of the polymer and the formation of the hollow tube or flat film. Alternatively, the fiberizing fluid temperature can be below the melted polymer temperature to assist in the formation and solidification of the nanofibers. The fiberizing fluid temperature is less than about 50° C. above the polymer melting point, preferably less than 25° C. above the polymer melting point, more preferably less than 15° C. above the polymer melting point, or just at or above the polymer melting point. The fiberizing fluid temperature may also be below the process temperature, down to 15° C. The pressure of the fiberizing fluid is sufficient to blow the nanofibers and can be slightly above the pressure of the melted polymer as it is extruded out of the orifice.

The fiberizing fluid will generally have a pressure below 5000 psi. Preferably, the fiberizing fluid pressure will be less than 1000 psi, more preferably less-than about 100 psi, and most preferably from about 15 to about 80 psi.

The polymer throughput will primarily depend upon the specific polymer used, the nozzle design, and the temperature and pressure of the polymer. The polymer throughput will be more than about 1 gram per minute per orifice. Preferably, the polymer throughput can be more than about 5 gram per minute per orifice and more preferably greater than about 10 gram per minute per orifice. There will likely be several orifices operating at one time which increases the total production throughput. The throughput, along with pressure, temperature, and velocity, are measured at the die orifice exit. Another way to describe the throughput is to use the term of extruded wet length. The polymer throughput will be more than about 0.3 gram per centimeter of extruded wet length. The extruded wet length is defined is the linear distance of the molten film before nanofibers are produced. For example, if the present invention is manifested using discrete nozzles and the nozzle orifice diameter is 1 centimeter, the mass throughput rate for that nozzle is 1 gram/minute, the overall rate is 0.318 gram per cm per minute. Preferably, the polymer throughput will be more than about 3 gram per cm per minute, more preferably greater than about 6 gram per cm per minute, and most preferably greater than 10 gram per cm per minute.

An entraining or other fluid may be used to induce a pulsating or fluctuating pressure field to help in forming a multiplicity of nanofibers. The entraining fluid can be provided by a transverse jet which is located to direct the flow of entraining fluid over and around the film and nanofiber forming region. The entraining fluid can have a velocity of from about 1 to about 100 meter per second and preferably from about 3 to about 50 meter per second. The temperature of the entraining fluid can be the same as the above fiberizing fluid, but it is typically about the same temperature as the melted polymer just as the film is formed. An air curtain or other ancillary air stream can also be used to affect the spray pattern of nanofibers from two or more nozzles. This air stream or curtain may aid in shielding the spray formations between adjacent nozzles or may aid in compressing the spray pattern. The air curtain or stream may improve the uniformity of the web.

Another fluid stream, a quench or heating fluid, can optionally be used. This third fluid stream can be located to direct fluid into the nanofibers to cool or heat the fibers. If the fluid is used as a quenching fluid, it is at a temperature of from about −20° C. to about 100° C. and preferably from about 10° C. to 40° C. If the fluid is used as a heating fluid, it is at a temperature of from about 40° C. to about 400° C. and typically from about 100° C. to about 250° C. Any fluid stream may contribute to the fiberization of the polymer melt and can thus generally be called fiberizing fluids. Any of the fluid streams may contain the treatments or additives for changing the surface, chemical, physical, or mechanical properties of fibers made.

The distance from the orifice or nozzle to collector distance, commonly called die-to-collector distance (DCD), can be optimized. The optimization may aid in producing a more uniform web. A reduction in the DCD may help to reduce the amount of fiber bundling or roping. This lower distance does not enable the fibers to have time to entangle, wrap around one another, or bundle. It may be desired to utilize more than one DCD for a web, to change the DCD during production, or to have different beams with different DCDs. It may be desirable to form a web with different uniformities by changing the DCD.

Nonlimiting examples of other nanofiber making processes from polymeric melts include melt fiber bursting, advanced melt blowing, and fibers splitting from multicomponent fibers and solid films. Examples of melt fiber bursting processes utilizing bursting polymer melt into fine fibers include U.S. Pat. No. 5,075,161 by Nyssen et al.; European Patent Nos. 1 192 301 B1 and 0 724 029 B1 and European Patent Application 1 358 369 A2 by Gerking; and WO 04/020722 by Sodemann et al. These methods utilize Laval nozzles to speed up the gas velocities to sonic and/or supersonic range. When polymer melt is exposed to such high gas velocities, it bursts into multiplicity of fine fibers.

Nyssen et al. disclose in U.S. Pat. No. 5,075,161 a method of bursting polyphenylene sulfide melt into fine filaments. In this method, the Laval nozzle is positioned just after the spinning nozzle. Polymer fibers having an average fiber diameter of less than about 6 microns, preferable from about 0.2 microns to 6 microns, are produced by subjecting the polymer melt streams to drawing out and cooling to below the melt temperature by extruding them into a gaseous medium which flows essentially parallel to the polymer melt streams and attains sonic or supersonic speed. This simultaneous deformation and cooling gives rise to amorphous fine or extremely fine fibers of finite length. High speed fiber bursting minimizes the surface oxidation of the fibers. WO 04/020722 by Sodemann et al. disclose a similar method of producing fine filament spunbonded nonwoven from fiber bursting of thermoplastic polymers by using sonic and supersonic fluid velocities. In said process, the Laval nozzle is placed underneath the spinning nozzle. The spinning speed, melt temperature, and the position of the Laval nozzle are appropriately set to achieve only partial thermal oxidation of fine filaments at their surface. The fibers produced by this method have been disclosed to have diameter of less than 1 micron, and are connected to one another at discrete points. Methods and apparatus disclosed by Gerking in European Patent Applications 1 192 301 B1 and 1 358 369 A2 also utilize Laval nozzle to speed up gas to sonic and supersonic velocity that is used to burst the polymer melt into multiplicity of fine filaments.

Melt film fibrillation process differs from melt fiber bursting process in how the fibers are made and the starting melt geometry from which fine filaments are produced. Melt film fibrillation starts with a film, in some instances a hollow melt film tube, that is thinned by central air jet and then fibrillates into multiplicity of nanofibers. In contrast, the starting melt geometry of melt bursting is a filament melt that when exposed to sonic and supersonic gas velocity in Laval nozzle bursts into multiplicity of nanofibers. Fibrous webs made from the processes may differ in uniformity because of differences in fiber-to-fiber separation and fiber bundle formations.

Various processes and combination of processes can be used to make the webs of the present invention. Preferred methods are methods which produce uniform nanofiber layers. Melt fiber bursting can be combined with melt film fibrillation with two separate beams on a single line. Various aspects of melt fiber bursting could be incorporated into melt film fibrillation. For example, fibers of different strengths and diameters could be produced to provide a desired combination of properties. Alternatively, aspects of melt film fibrillation can be included in other melt fibrillation processes to increase the throughput rate by utilizing a hollow elongated tube to form fibers. For example, a melt film fibrillation process could be modified to include a Laval nozzle to aid in drawing down the fibers. Drawing down can aid in further attenuation and increase the strength of the fibers. This may be particularly preferred for high Tg polymers such as polyesters where crystallization is stress induced.

The nanofibers of the present invention are used to make nonwoven webs suitable for barrier properties in articles.

The web is defined as the total nonwoven composite. A web may have one or several layers which are consolidated by thermal point-bonding or other techniques to attain strength, integrity and certain aesthetic characteristics. A layer is the web or part of a web that is produced in a separate fiber lay down or forming step. The webs of the present invention will comprise one or more layers having a significant number of nanofibers having diameters of less than one micron. A significant number is defined as at least about 25%. The significant number of fibers can be at least about 35%, at least about 50%, or more than about 75% of the total number of fibers in the layer. The web could have more than about 90% or about 100% of the fibers having a diameter of less than about one micron. The fiber diameters of the web are measured using a scanning electron microscope at a magnification of greater than about 500 times and up to about 10,000 times as needed for visual analysis. To determine if a significant number of fibers have diameters less than one micron, at least about 100 fibers and preferably more fibers must be measured. The measurements must occur at various regions throughout the layer. Sufficient sampling that is statistically significant must occur.

The fiber diameter of the remaining larger fibers in the nanofiber layer, up to 75%, may have fiber diameters in any range. Typically, the larger fiber diameters will be just above one micron to about 10 microns.

Preferably, a significant number of fibers in a nanofiber layer will have a fiber diameter of less than about 900 nanometers and more preferably from about 100 nanometers to about 900 nanometers. Other preferably ranges of fiber diameter are less than about 700 nanometers and from about 300 to about 900 nanometers. The preferred diameters depend upon the use of the web. It may be desirable to have a significant number of fibers having a diameter of less than about one micron and a significant number of fibers having a diameter of great than about one micron. The larger fibers may trap and immobilize the nanofibers. This may help to reduce the amount of clumping or roping of the nanofibers and prevent the nanofibers from being carried off by stray air currents.

The layer of nanofibers in a web of the present invention may contain more than one polymer. Different polymers or polymer blends may be used for different orifices to produce layers in a web having different fiber diameters and different polymer compositions.

It may be desirable to produce a single layer nonwoven with varying fiber diameters. Alternatively, it can be desired to produce a nonwoven web with multiple layers with each layer having different fiber diameters. The melt film fibrillation process can be modified to produce both small and large diameter fibers to make various webs. The smaller fiber diameters are referred to as having a significant number of fibers having a diameter of less than one micron. The larger diameter fibers include fibers from the melt blowing range (typically 3 to 5 microns) to the spunbond (typically around 10 microns) or any range of fiber diameters above 1 micron. For example, one layer can be produced with an average fiber diameter of less than one micron and another layer with an average fiber diameter of around 5 microns. This type of structure could be used where traditionally spunbond-meltblown-spunbond (SMS) webs are used. The webs with various fiber diameters can be produced on the same line with the same equipment. This is an inexpensive way as the same equipment and components can be used. The operating costs and equipment costs are both controlled. Also, if desired, the same polymer can be used to produce different fiber diameters.

The articles of the present invention will contain the described nonwoven webs. The web may comprise the entire articles, such as a wipe, or the web may comprise one component of the article, such as a diaper. Hygiene articles are preferred articles. The hygiene articles include diapers, training pants, adult incontinence pads, catamenials products such as feminine care pads and pantiliners, tampons, personal cleansing articles, personal care articles, and personal care wipes including baby wipes, facial wipes, body wipes, and feminine wipes. Personal care articles include articles such as wound dressings, active delivery wraps or patches, and other substrates that are applied to the body, particularly the skin. Disposable underwear or clothing and protective wear for personal or industrial uses may also be desired. Other uses of wipes can be clean room wipes or decontamination wipes for use to absorb or control spills and other industrial wipes.

In a diaper, the web may be used as a barrier layer such as a barrier-on-core or an outercover. The webs may also be used as a high barrier cuff with a high hydrostatic head to enable low leakage incident rates of thin, narrow crotch diapers desired for comfort and fit. A typical web utilizing nanofibers is a web wherein the nanofiber layer is combined with at least one spunbond layer and consolidated using thermal point-bonding, hydro-entangling or other techniques suitable and appropriate for the end-use. There may be one or two spunbond layers encompassing the nanofiber layer.

In a diaper or other disposable absorbent product, the nonwoven web containing nanofibers may be utilized as a barrier layer. The barrier layer may be disposed between an absorbent core and an outer layer containing a garment. The absorbent core is the component of the article that is primarily responsible for fluid handling properties such as acquiring, transporting, distributing, and storing body fluids. The absorbent core is typically located between a liquid pervious body-side inner layer and a vapor permeable, liquid impermeable outer cover. The outer layer, also known as the back sheet or outer covering, is located on the outside of the disposable product. In the case of a diaper, the outer layer contacts the user's garment or clothing. The barrier layer may alternatively or also be disposed between the absorbent core and an inner layer. The inner layer, also known as a top sheet, is located on the side closest to the user's skin. The inner layer may contact the user's skin or may contact a separate top sheet with contacts the user's skin. The barrier layer may be absorbent. The barrier layer most preferably has a balance between convective air flow and absorptive barrier property. The convective air flow property is effective to reduce the relative humidity within the space between the absorbent article and the wearer's skin. The combination of liquid absorption and liquid barrier property provides protection against the wet through problem and is especially beneficial when the absorbent article is under impact and/or sustained pressure. Further description and benefits of the barrier layers may be found in WO 01/97731.

The webs may be used in wipes to enable improved lotion handling and reduced gradient of liquids. The webs may also provide controlled delivery of a substance. The delivered substance can be of liquids, lotions, actives, or other materials. Due to the high surface area of the nanofibers, the webs may be used as absorbent materials for wipes or cores of feminine care product pads, diapers, training pants, or adult incontinence. The webs may provide enhanced distribution of fluids and/or retention. Additionally, the webs for absorbent uses may be made with added particulates or absorbent or natural fibers for increased absorbance or certain layers of the webs may have different properties.

The nanofiber webs may also be used in articles wherein opaqueness is desired. Added opaqueness may result due to the small fiber diameter and uniformity or pigments may be added to the polymer melt or webs. The webs have also been found to have low linting. This may be due to longer length fibers or entangling of fibers in the web.

Other products that will benefit from a nanofiber web include filters. Filters can be for industrial, personal, or home use and can be used to filter air, liquids, or small particles. Industrial uses can include automotive, furnace, water, and other types of filters. A type of personal filter includes a filter mask such as a surgical mask. Other medical uses of webs containing nanofiber layers include surgical gowns, wound dressings, and medical barriers. The webs can also be used as noise and thermal insulators, for outdoor gear, clothing, and as conducting fibers.

TEST METHODS

Air Permeability

The air permeability is determined by measuring the time in which a standard volume of air is drawn through the test specimen at a constant pressure and temperature. This test is particularly suited to materials having relatively high permeability to gases, such as nonwovens, apertured films and the like. A TexTest FX3300 instrument is used. (Available by Textest AG in Switzerland (www.textest.ch), or from Advanced Testing Instruments in Spartanburg S.C., USA.) The Test Method conforms to ASTM D737. The test is operated in a laboratory environment at about 22±2° C. and about 50% relative humidity. The test pressure is 125 Pascal and the test area is 38 cm$^2$. In this test, the instrument creates a constant differential pressure across the sample which draws air through the sample. The rate of air flow through the sample is measured in ft$^3$/ft$^2$/min (often called cfm or ft/min) or m/min. For each sample, three replicates should be run, and the average result is reported.

Hydrostatic Head (Hydrohead) Pressure or Repellency Test

The property determined by this test is a measure of the liquid barrier property (or liquid impermeability) of a material. Specifically, this test measures the hydrostatic pressure the material will support when a controlled level of water penetration occurs. A TexTest Hydrostatic Head Tester FX3000 (available from Advanced Testing Instruments, Corp., Spartanburg, S.C., or by Textest AG in Switzerland (www.textest.ch)) is used. The test method conforms to EDANA 120.2-02 and INDA 80.6. For this test, pressure is applied to a defined sample portion and gradually increases until water penetrates through the sample. The test is conducted in a laboratory environment at about 22±2° C. temperature and about 50% relative humidity. The sample is clamped over the top of the column fixture, using an appropriate gasketing material (o-ring style) to prevent side leakage during testing. The area of water contact with the sample is equal to the cross sectional area of the water column, which equals 28 cm$^2$. Water is pumped into the water column at a rate of 3 mbar/min. Thus, the sample is subjected to a steadily increasing water pressure on one surface. When water penetration appears in three locations on the other surface of the sample, the pressure at which the third penetration occurs is recorded. If water immediately penetrates the sample (i.e., the sample provided no resistance), a zero reading is recorded. For each material, three specimens are tested and the average result is reported.

Basis Weight or Grammage

Basis weight can be measured consistent with compendial methods ASTM D 756, ISO 536 and EDANA ERT40.3-90. Basis weight is defined as mass per unit area, with grams per square meter (often called gsm rather than g/m$^2$) as the preferred unit. Required instruments are a scissors or a die-cutter for sample cutting and an accurate weighing device (scale). A sample is cut to a total area of 100 cm$^2$ per layer with an accuracy and precision of ±0.5%. A scale or balance is needed with 0.001 g sensitivity, readable, calibrated and accurate to within 0.25% of the applied load. The samples are conditioned at 23° Celsius (±2° C.) and at a relative humidity of about 50% for 2 hours to reach equilibrium. Weigh the cut sample with 10 plies from the sample area for a total of 1000 cm$^2$=0.1 m$^2$ on an analytical balance to the nearest 0.001 g and record the weight. (For samples thicker than 1 mm, weighing only 1 plie is preferred but should be noted if done so.) Calculate the basis weight by dividing the weight by the sample area (all layers tested) to give the basis weight in gsm. All data are recorded for statistic analysis.

Fiber Diameter (and Denier)

Fiber diameters are determined by using a Scanning Electron Microscope (SEM) and image analysis software. A magnification of 500 to 10,000 is chosen such that the fibers (or filaments) are suitably enlarged for measurements. Image analysis software for automatic sampling of fiber diameter in the SEM picture is possible, but also a more manual procedure can be used. In principle the edge of a randomly selected fiber is sought and then measured across the width (perpendicular to fiber direction at that spot) to the other edge of the fiber. A scaled and calibrated image analysis tool provides the scaling to get the actual reading in meter or mm or micrometers (μm), e.g. Several fibers or filaments are thus randomly selected across the sample of web in the SEM. Typically several samples from a web are cut and tested in this manner. Altogether at least about 100 such measurements are made and all data are recorded for statistic analysis. If the result is to be recorded in denier, then the following calculation needs to be made. Diameter in denier=Cross-sectional area*density*9000 m*1000 g/kg. The cross-sectional area is π*diameter$^2$/4. The density for PP, e.g., can be taken as 910 kg/m$^3$. To obtain decitex (dtex), instead of using 9000 m, use 10,000 m.

EXAMPLES

Samples have been prepared using several technologies and evaluated with the described methods. The samples are composites of extrudable polypropylene of one or more nanofiber layers and adjacent larger diameter fibrous layers. Furthermore, all the composites were consolidated or bonded using a thermal pointbonding process. Basis weights and fiber diameters are given as average data.

| Sample Type | Composite | Large diameter fibrous layers | Nanofiber layers |
| --- | --- | --- | --- |
| 1 | SMS, SM | Diameters 12–20 micron; basis weights 5–20 gsm per S-layer | Diameters of 0.7 to 4 micron; basis weights 2 to 20 gsm. |

-continued

| Sample Type | Composite | Large diameter fibrous layers | Nanofiber layers |
|---|---|---|---|
| 2 | SN | Diameters 12–20 micron, basis weights 10–15 gsm | Diameters of 0.5 to 0.9, basis weighs of 0.5 to 22 gsm. |
| 3 | Spunbond-Electrospun composite ("Electrospun") | Diameters of 15–20 micron, basis weights 10–15 gsm | Diameters of 0.1 to 0.3 micron, basis weights of 2 and 3 gsm. (2 samples) |

Of every sample type, various samples were made at the different basis weights listed (according to line speed), and then tested for fiber size, hydrostatic head and air permeability according to the methods described. The hydrostatic head for the "electrospun sample" was predicted by comprehensive computer modeling based on Laplace equation. Surface energy of polypropylene was used. Other web characteristics such as fiber size, basis weight, and caliper were acquired from electrospun Nylon-6 with average fiber diameters from 0.1 to 0.3 microns. To give the effectiveness of the nanofiber layers in the composites, the hydrostatic head result can be divided by the basis weight of the nanofiber layer. Giving one of the samples as a comparative example for sample type 1, the SMS is made as known to those skilled in the art, is a composite with basis weight for the S/M/S layers of 13.5/3/13.5 gsm, with the S-layer diameter being around 18 micron and the M-layer diameter being around 2 micron. The above chart shows the several samples and basis weights of the nanofiber layer and diameters of the nanofiber layers.

Figure 1:
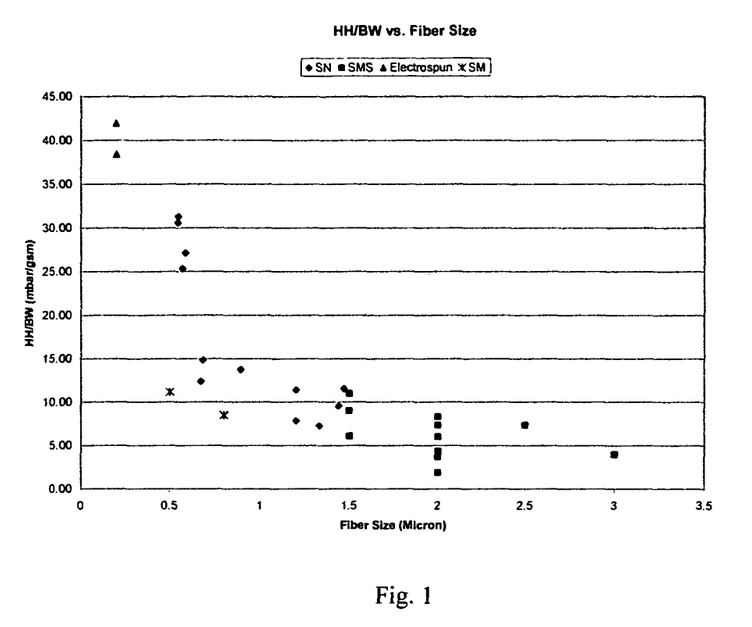
FIG. 1 is a chart showing hydrohead/basis weight ratio for various fiber sizes.

FIG. 1 is a chart graphing hydrohead/basis weight versus fiber diameter size. As can be seen, the finer the diameter of the fibers in the nanofiber layers, the higher the hydrostatic head result, when normalized by basis weight.

Figure 2:
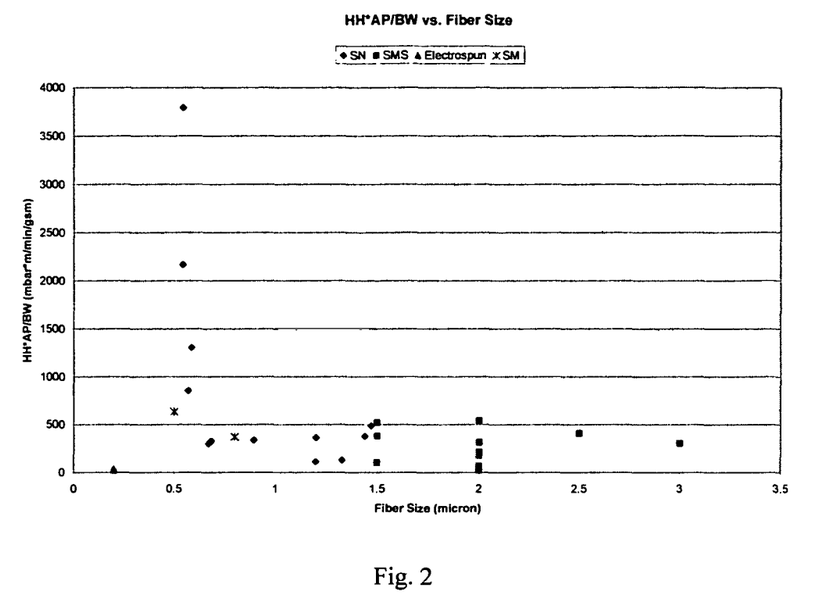
FIG. 2 is a chart showing hydrohead×air permeability/basis weight for various fiber sizes.

In FIG. 2, the samples of the examples are evaluated for a combined product of gas permeability (air permeability method) and liquid barrier (using hydrostatic head method). The chart graphs hydrohead×air permedability/basis weight versus fiber diameter size. The important observation is that an optimum can be reached within a certain fiber diameter range. The method of creating fibers of that diameter may not be critical, but the final diameter is important.

Samples that exhibit similar trends can be prepared using other technologies, such as composites comprising fibrous webs from other melt fibrillation processes, such as for example using islands-in-the-sea.

A preferable diameter for fibers in the nanofiber layers to attain an optimal high liquid-barrier and gas-permeability product is between 0.1 and about 1 micrometer, and most preferably between 0.3 and 0.7 microns. Alternatively, the respective pore size diameter can be used to describe this range.

Without being bound by theory, it is believed that there is an optimal fiber size for barrier and air permeability performance. For larger pore sizes, surface tension dominates the barrier performance. For medium pore sizes, surface tension and drag forces both affect barrier performance. For very small pore size (for nanofibers), drag forces dominate the barrier performance. The barrier to liquid increases to a larger degree than the barrier to air with a decrease in pore size as liquid drag increases at a faster rate than air drag. Therefore, an optimal fiber diameter size can be found where air permeability is not significantly reduced but liquid barrier performance is high. Drag forces, as used herein, refer to frictional drag forces.

All documents cited are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven web comprising:
a first layer of spunbond fibers;
a second layer of spunbond fibers; and
at least one nanofiber layer disposed between said first and second layers of spunbond fibers, said nanofiber layer comprising at least 50% nanofibers with a diameter ranging from 500-900 nanometers, said nanofiber layer having a basis weight of less than about 25 gsm, a mean pore diameter of less than about 15 microns, and a coefficient of variation in at least one of the following of less than 20%: pore diameter, basis weight, air permeability, and/or opacity; wherein the nonwoven web has a hydrohead greater than 10 mbar and air permeability greater than 1 m/min, wherein a product of the hydrohead and the air permeability divided by the basis weight is greater than about 500 mbar*meter per minute per gsm.

2. The nonwoven web of claim 1 wherein the product of the hydrohead and the air permeability divided by the basis weight is greater than about 750 mbar*meter per minute per gsm.

3. The nonwoven web of claim 1 wherein the nanofiber layer has a basis weight of from about 0.5 gsm to about 3 gsm.

4. The nonwoven web of claim 1 wherein the nanofiber layer has a basis weight of from about 3 gsm to about 15 gsm.

5. A nonwoven web comprising:
a first layer of spunbond fibers;
a second layer of spunbond fibers; and
at least one nanofiber layer disposed between said first and second layers of spunbond fibers, said nanofiber layer having at least 50% nanofibers with a diameter ranging from 500 to 900 nanometers, a basis weight of less than about 25 gsm, and a mean pore diameter of less than about 15 microns, wherein the nonwoven web has a hydrohead to nanofiber layer basis weight ratio of at least 10 mbar/gsm and an air permeability of at least 15 meter per minute wherein a product of hydrohead and air permeability divided by basis weight is at least 500 mbar*meter per minute per gsm.

6. The nonwoven web of claim 5 wherein the nonwoven web has a hydrohead to nanofiber layer basis weight ratio of at least 20 mbar/gsm and an air permeability of at least 75 meters per minute.

7. The nonwoven web of claim 5 wherein the basis weight of the nonwoven web is from about 0.5 gsm to about 15 gsm.

8. The nonwoven web of claim 5 wherein the product of hydrohead and air permeability is at least 750 mbar*meter per minute.

9. An article comprising a nonwoven web of claim 1.

10. The article of claim 9 wherein the article is selected from the group consisting of diapers, training pants, adult incontinence pads, catamenials products such as feminine care pads and pantiliners, tampons, personal cleansing articles, personal care articles, and personal care wipes such as baby wipes, facial wipes, body wipes and feminine wipes, and combinations thereof.

11. The article of claim 10 wherein the nonwoven web is a liquid barrier layer.

12. The article of claim 11 wherein the barrier layer is disposed between an absorbent core and an outer layer contacting a garment or is disposed between an absorbent core and an inner layer contacting a user's skin.

13. The article of claim 11 wherein the nonwoven web is surface coated to improve barrier performance.

14. An article comprising a nonwoven web of claim 5 wherein the article is selected from the group consisting of diapers, training pants, adult incontinence pads, catamenials products such as feminine care pads and pantiliners, tampons, personal cleansing articles, personal care articles, and personal care wipes such as baby wipes, facial wipes, body wipes and feminine wipes, and combinations thereof.

15. The article of claim 14 wherein the nonwoven web is a liquid barrier layer.

16. The article of claim 15 wherein the barrier layer is disposed between an absorbent core and an outer layer contacting a garment or is disposed between an absorbent core and an inner layer contacting a user's skin.

17. A nonwoven web comprising:
a first layer of spunbond fibers;
a second layer of spunbond fibers; and
at least one nanofiber layer disposed between said first and second layers of spunbond fibers, said nanofiber layer having at least 50% nanofibers with a diameter ranging from 500 to 900 nanometers, a basis weight of from about 0.1 gsm to about 15 gsm, and a mean pore diameter of less than 15 microns, wherein the nonwoven web has a hydrohead to the nanofiber layer basis weight ratio of greater than about 10 mbar/gsm, an air permeability of at least 15 meter per minute and a product of hydrohead and air permeability divided by basis weight of at least 500 mbar*meter per minute per gsm.

18. The nonwoven web of claim 1 wherein the nanofiber layer has a basis weight of from about 0.5 gsm to about 1.5 gsm.

19. The nonwoven web of claim 1 comprising larger fibers having diameters ranging from above 1 micron to about 10 microns.

20. The nonwoven web of claim 19 wherein the nanofibers and larger fibers are in a single layer.

21. The nonwoven web of claim 19 wherein the nanofibers and larger fibers are in different layers.

22. The nonwoven web of claim 1 wherein the nanofiber layer has a coefficient of variation in pore diameter of less than 20%.

23. A nonwoven web comprising:
a first layer of spunbond fibers;
a second layer of spunbond fibers; and
at least one nanofiber layer disposed between said first and second layers of spunbond fibers, said nanofiber layer comprising at least 90% nanofibers with a diameter ranging from 500-900 nanometers and larger fibers having diameters ranging from above 1 micron to about 10 microns, said layer having a basis weight of less than about 10 gsm, a coefficient of variation in basis weight of less than 20%, and a mean pore diameter of less than about 15 microns.

24. A nonwoven web comprising at least one nanofiber layer having at least 50% nanofibers with a diameter ranging from 500-900 nanometers, a basis weight of less than about 25 gsm, and a mean pore diameter of less than about 15 microns, wherein the nonwoven web has a hydrohead and air permeability wherein a product of the hydrohead and the air permeability divided by the basis weight is greater than about 500 mbar*meter per minute per gsm, and where the at least one nanofiber layer is adjacent at least one large fiber diameter layer with the large fiber diameters between 12 and 20 micron.

25. The nonwoven web of claim 24 where the sum of the basis weights of one or more adjacent large fiber diameter layer is from 5 to 20 gsm.

26. The nonwoven web of claim 24 where the sum of the basis weights of one or more adjacent large fiber diameter layer is from 5 to 15 gsm.

27. The nonwoven web of claim 24 wherein the nanofiber layer has a basis weight of from about 0.5 gsm to about 1.5 gsm.

28. The nonwoven web of claim 1 wherein the nanofiber layer has a coefficient of variation in basis weight of less than 20%.

29. The nonwoven web of claim 1 wherein the nanofiber layer has a coefficient of variation in air permeability of less than 20%.

30. The nonwoven web of claim 1 wherein the nanofiber layer has a coefficient of variation in opacity of less than 20%.

31. The nonwoven web of claim 1 wherein the nanofiber layer comprises a melt fibrillated layer.

32. The nonwoven web of claim 1 wherein the nanofiber layer comprises a melt film fibrillated layer.

33. The nonwoven web of claim 31 wherein the nanofibers are comprised of a composition selected from the group consisting of at least one of: polypropylene and polyethylene.

34. An article comprising the nonwoven web of claim 1 wherein the article is selected from the group consisting of diapers, training pants, adult incontinence pads, catamenials products such as feminine care pads and pantiliners, and tampons.

35. A diaper according to claim 34 wherein the nonwoven web is in a barrier cuff.

36. The nonwoven web of claim 23 wherein the larger fibers have diameters ranging from 6 microns to about 10 microns.

37. A nonwoven web comprising:
a first layer of spunbond fibers;
a second layer of spunbond fibers; and
at least one melt fibrillated nanofiber layer disposed between said first and second layers of spunbond fibers, said nanofiber layer comprising at least 50% nanofibers with a diameter ranging from 500-900 nanometers, wherein said nanofibers comprise at least one of: polypropylene and polyethylene, wherein said nanofiber layer a basis weight of less than about 25 gsm, and a mean pore diameter of less than about 15 microns, wherein the nonwoven web has a hydrohead greater than 10 mbar and air permeability greater than 1 m/min, wherein a product of the hydrohead and the air permeability divided by the basis weight is greater than about 500 mbar*meter per minute per gsm.

38. The nonwoven web of claim 1 which is consolidated by thermal point bonding.

* * * * *